United States Patent
Xie et al.

(10) Patent No.: US 10,415,103 B2
(45) Date of Patent: Sep. 17, 2019

(54) GEXP RAPID DETECTION PRIMER SET FOR SIMULTANEOUSLY IDENTIFYING GENE HA OF EIGHT DIFFERENT HUMAN-INFECTED SUBTYPES OF AVIAN INFLUENZA VIRUS, KIT AND USE THEREOF

(71) Applicant: Guangxi Veterinary Research Institute, Nanning (CN)

(72) Inventors: Zhixun Xie, Nanning (CN); Meng Li, Nanning (CN); Zhiqin Xie, Nanning (CN); Sisi Luo, Nanning (CN); Liji Xie, Nanning (CN); Li Huang, Nanning (CN); Xianwen Deng, Nanning (CN); Jiaoling Huang, Nanning (CN); Qing Fan, Nanning (CN); Yanfang Zhang, Nanning (CN); Tingting Zeng, Nanning (CN); Sheng Wang, Nanning (CN)

(73) Assignee: Guangxi Veterinary Research Institute, Nanning (CN)

( * ) Notice: Subject to any disclaimer, the term of this patent is extended or adjusted under 35 U.S.C. 154(b) by 197 days.

(21) Appl. No.: 15/361,964

(22) Filed: Nov. 28, 2016

(65) Prior Publication Data

US 2017/0152577 A1    Jun. 1, 2017

(30) Foreign Application Priority Data

Nov. 27, 2015   (CN) .......................... 2015 1 0843579

(51) Int. Cl.
| | | |
|---|---|---|
| *C12Q 1/68* | (2018.01) | |
| *C12P 19/34* | (2006.01) | |
| *C12Q 1/70* | (2006.01) | |

(52) U.S. Cl.
CPC .......... *C12Q 1/701* (2013.01); *C12Q 2600/16* (2013.01)

(58) Field of Classification Search
None
See application file for complete search history.

(56) References Cited

FOREIGN PATENT DOCUMENTS

| CN | 105200049 A | 12/2015 |
|---|---|---|
| CN | 105316430 A | 2/2016 |
| CN | 105349698 A | 2/2016 |

*Primary Examiner* — Young J Kim
(74) *Attorney, Agent, or Firm* — The Webb Law Firm (57) ABSTRACT

Provided herein are a GeXP rapid detection primer set for simultaneously identifying gene HA of eight different human-infected subtypes of avian influenza virus, a kit, and use thereof. Disclosed are 9 pairs of specific primer and 1 pair of universal primer, for a GeXP rapid detection primer kit for simultaneously identifying gene HA of eight different human-infected subtypes of avian influenza virus. Eight different human-infected subtypes HA of avian influenza virus from the nine genes of M, H1, H2, H3, H5, H6, H7, H9 and H10 can be identified simultaneously with a sensitivity of $10^2$ copies/μL.

3 Claims, 2 Drawing Sheets

Specification includes a Sequence Listing.

SEQUENCE LISTING

```
<160> NUMBER OF SEQ ID NOS: 20

<210> SEQ ID NO 1
<211> LENGTH: 35
<212> TYPE: DNA
<213> ORGANISM: Artificial Sequence
<220> FEATURE:
<223> OTHER INFORMATION: Avian influenza primer A1

<400> SEQUENCE: 1
aggtgacact atagaataag ccgagatcgc gcaga                              35

<210> SEQ ID NO 2
<211> LENGTH: 36
<212> TYPE: DNA
<213> ORGANISM: Artificial Sequence
<220> FEATURE:
<223> OTHER INFORMATION: Avian influenza primer A2

<400> SEQUENCE: 2
gtacgactca ctatagggac gctcactggg cacggt                             36

<210> SEQ ID NO 3
<211> LENGTH: 40
<212> TYPE: DNA
<213> ORGANISM: Artificial Sequence
<220> FEATURE:
<223> OTHER INFORMATION: Avian influenza primer B1

<400> SEQUENCE: 3
aggtgacact atagaatacc agaaygtgca tcctatcact                         40

<210> SEQ ID NO 4
<211> LENGTH: 41
<212> TYPE: DNA
<213> ORGANISM: Artificial Sequence
<220> FEATURE:
<223> OTHER INFORMATION: Avian influenza primer B2

<400> SEQUENCE: 4
gtacgactca ctatagggat atcattcctg tccawccccc t                       41

<210> SEQ ID NO 5
<211> LENGTH: 41
<212> TYPE: DNA
<213> ORGANISM: Artificial Sequence
<220> FEATURE:
<223> OTHER INFORMATION: Avian influenza primer C1

<400> SEQUENCE: 5
aggtgacact atagaatatt cgagaaagtr aagattytgc c                       41
```

<210> SEQ ID NO 6
<211> LENGTH: 80
<212> TYPE: DNA
<213> ORGANISM: Artificial Sequence
<220> FEATURE:
<223> OTHER INFORMATION: Avian influenza primer C2

<400> SEQUENCE: 6
gtacgactca ctatagggac cagaccatgt tcctgaagaa gtacgactca ctatagggac 60
cagaccatgt tcctgaagaa 80

<210> SEQ ID NO 7
<211> LENGTH: 43
<212> TYPE: DNA
<213> ORGANISM: Artificial Sequence
<220> FEATURE:
<223> OTHER INFORMATION: Avian influenza primer D1

<400> SEQUENCE: 7
aggtgacact atagaatatt gccatatcat gytttttgct ttg 43

<210> SEQ ID NO 8
<211> LENGTH: 44
<212> TYPE: DNA
<213> ORGANISM: Artificial Sequence
<220> FEATURE:
<223> OTHER INFORMATION: Avian influenza primer D2

<400> SEQUENCE: 8
gtacgactca ctatagggaa atgcaaatgt tgcacctaat gttg 44

<210> SEQ ID NO 9
<211> LENGTH: 42
<212> TYPE: DNA
<213> ORGANISM: Artificial Sequence
<220> FEATURE:
<223> OTHER INFORMATION: Avian influenza primer E1

<400> SEQUENCE: 9
aggtgacact atagaatagg aaagtgtaag aaacggaacg ta 42

<210> SEQ ID NO 10
<211> LENGTH: 42
<212> TYPE: DNA
<213> ORGANISM: Artificial Sequence
<220> FEATURE:
<223> OTHER INFORMATION: Avian influenza primer E2

<400> SEQUENCE: 10
gtacgactca ctatagggac acatccataa agayagacca gc 42

<210> SEQ ID NO 11
<211> LENGTH: 38
<212> TYPE: DNA
<213> ORGANISM: Artificial Sequence
<220> FEATURE:
<223> OTHER INFORMATION: Avian influenza primer F1

<400> SEQUENCE: 11
aggtgacact atagaatatc tcaaacaagg cccctctc 38

<210> SEQ ID NO 12
<211> LENGTH: 39
<212> TYPE: DNA
<213> ORGANISM: Artificial Sequence
<220> FEATURE:

<223> OTHER INFORMATION: Avian influenza primer F2

<400> SEQUENCE: 12
gtacgactca ctatagggat cccatttcgg gcattaggc                              39

<210> SEQ ID NO 13
<211> LENGTH: 41
<212> TYPE: DNA
<213> ORGANISM: Artificial Sequence
<220> FEATURE:
<223> OTHER INFORMATION: Avian influenza primer G1

<400> SEQUENCE: 13
aggtgacact atagaataag aatacagatt gacccagtsa a                           41

<210> SEQ ID NO 14
<211> LENGTH: 39
<212> TYPE: DNA
<213> ORGANISM: Artificial Sequence
<220> FEATURE:
<223> OTHER INFORMATION: Avian influenza primer G2

<400> SEQUENCE: 14
gtacgactca ctatagggac ccattgcaat ggchagaag                              39

<210> SEQ ID NO 15
<211> LENGTH: 40
<212> TYPE: DNA
<213> ORGANISM: Artificial Sequence
<220> FEATURE:
<223> OTHER INFORMATION: Avian influenza primer H1

<400> SEQUENCE: 15
aggtgacact atagaataac catttattcg actgtcgcct                             40

<210> SEQ ID NO 16
<211> LENGTH: 38
<212> TYPE: DNA
<213> ORGANISM: Artificial Sequence
<220> FEATURE:
<223> OTHER INFORMATION: Avian influenza primer H2

<400> SEQUENCE: 16
gtacgactca ctatagggac attggacatg gcccagaa                               38

<210> SEQ ID NO 17
<211> LENGTH: 35
<212> TYPE: DNA
<213> ORGANISM: Artificial Sequence
<220> FEATURE:
<223> OTHER INFORMATION: Avian influenza primer I1

<400> SEQUENCE: 17
aggtgacact atagaataaa cacggacacr gctga                                  35

<210> SEQ ID NO 18
<211> LENGTH: 39
<212> TYPE: DNA
<213> ORGANISM: Artificial Sequence
<220> FEATURE:
<223> OTHER INFORMATION: Avian influenza primer I2

<400> SEQUENCE: 18
gtacgactca ctatagggaa ttgttctggt awgtggaac                              39

```
<210> SEQ ID NO 19
<211> LENGTH: 18
<212> TYPE: DNA
<213> ORGANISM: Artificial Sequence
<220> FEATURE:
<223> OTHER INFORMATION: Universal primer Cy5-Tag-F

<400> SEQUENCE: 19
aggtgacact atagaata                                                 18

<210> SEQ ID NO 20
<211> LENGTH: 19
<212> TYPE: DNA
<213> ORGANISM: Artificial Sequence
<220> FEATURE:
<223> OTHER INFORMATION: Universal primer Tag-R

<400> SEQUENCE: 20
gtacgactca ctataggga                                                19
```

GEXP RAPID DETECTION PRIMER SET FOR SIMULTANEOUSLY IDENTIFYING GENE HA OF EIGHT DIFFERENT HUMAN-INFECTED SUBTYPES OF AVIAN INFLUENZA VIRUS, KIT AND USE THEREOF

CROSS-REFERENCE TO RELATED APPLICATION

This application claims priority of Chinese Patent Application No. 201510843579.2, filed Nov. 27, 2015, the disclosure of which is hereby incorporated in its entirety by reference.

The Sequence Listing associated with this application is filed in electronic format via EFS-Web and is hereby incorporated by reference into the specification in its entirety. The name of the text file containing the Sequence Listing is 1604376_ST25.txt. The size of the text file is 4,418 bytes, and the text file was created on Sep. 23, 2016.

TECHNICAL FIELD

The present invention relates to the field of avian virus detection technology, in particular relates to GeXP rapid detection primer set for simultaneously identifying gene HA of eight different human-infected subtypes of avian influenza virus, kit and use thereof.

BACKGROUND

At present influenza virus is one of main pathogenic microorganisms harmful to human health, which not only causes great economic loss, but also affects the society stability. The natural host of influenza virus is avian, and the avian influenza virus can break through barrier between species to infect people. So far, type A influenza virus which can infect human and cause human influenza pandemic or seasonal influenza can only be subtype H1N1, subtype H2N2 or subtype H3N2 of influenza virus. From the origin, human influenza viruses are all derived from avian influenza virus. In recent years, subtype H5 of highly pathogenic avian influenza often breaks out in poultry causing huge economic loss, and occasionally infects humans causing concentrated infections or sporadic cases in some areas. In February 2013, a new type of human-infected H7N9 avian influenza virus appeared in Anhui and Shanghai of China, which had caused 571 cases of human infection and had leaded to 212 cases of death till Feb. 23, 2015. Subtype H9N2 of influenza virus is a kind of low pathogenic influenza virus, which is common in poultry. In recent years, subtype H9N2 of influenza virus has been isolated incessantly from samples of infected patients. As early as 2004, the first case of human infection with subtype H10N7 of avian influenza virus was reported in Egypt. In Australia the cases of human infection with subtype H10N7 of virus also occurred in 2010 and 2012. In December 2013, the first case of human infection with H10N8 avian influenza virus appeared in Jiangxi province of China. In June 2013, the world's first case of human infection with subtype H6N1 of avian influenza virus was detected in Taiwan, whose viral gene sequence isolated from the patient showed that the virus was of typically low pathogenic avian influenza virus. The above studies show that there are at least eight different human-infected subtypes H1, H2, H3, H5, H6, H7, H9 and H10 of avian influenza virus.

At present, laboratory detection techniques for avian influenza virus mainly include methods like virus isolation and culture thereof, serological experiment, molecular biology experiment and immunofluorescence etc., wherein virus isolation and culture thereof are "gold standard" for the diagnosis of avian influenza virus infection. Due to various subtypes of avian influenza and many emerging variants, using the above detecting method for classifying and diagnosing avian influenza virus not only has the disadvantage of complicated operation, but also has the disadvantages of long detection period and accurate and not timely detection results easily affected by antibody etc. Although multiplex PCR has advantage of simultaneous amplification of multiple target fragments so as to realize rapid diagnosis of various kinds of pathogens and has advantage of reduced detection cost, common multiplex PCR in the amplification process are susceptible to characteristic of target gene template, primer concentration, primer proportion and interaction between PCR reagents, leading to different amplification efficiency of samples which has accuracy of detection results reduce greatly. Multiplex reverse transcription polymerase chain reaction (mRT-PCR) in GeXP multiplex gene genetic expression analysis system can solve problem of different amplification efficiency present in the common multiplex PCR by combining universal primer (labeled with fluorescent marker upstream) and specific chimeric primer (5' end of gene specific primer is connected with universal primer sequence) to build multiplex reverse transcription polymerase chain reaction system and then using strategy of universal primer initiation. In addition, this method makes use of capillary electrophoresis to separate product, which greatly improves the sensitivity and reliability of detection result.

Currently nucleic acid detection method for detecting different subtypes of avian influenza virus is used for detecting simultaneously three different subtypes HA at most, while detection technique which can detect simultaneously eight different human-infected subtypes HA of avian influenza virus like H1, H2, H3, H5, H6, H7, H9 and H10 in one reaction has not been reported yet.

Information disclosed in the background is simply used for better comprehension of overall background of the present invention, while should not be considered as acknowledging or implying in any form that the information is general prior art for a person skilled in the art.

SUMMARY OF THE INVENTION

In order to overcome the disadvantages of the prior art, GeXP multiplex PCR technique established in the present invention provides method of multiplex reverse transcription polymerase chain reaction (mRT-PCR) which can detect simultaneously gene HA of eight different human-infected subtypes of avian influenza virus from nine genes of M, H1, H2, H3, H5, H6, H7, H9 and H10 by one PCR reaction in four hours. The method is used to detect eight different subtypes HA of avian influenza virus and perform genotyping thereof for the goal of rapid diagnosis and discrimination of different humans-infected subtypes of avian influenza virus. The method has great significance for the epidemiological investigation of human-infected avian influenza virus, prevention and control thereof, and it is also important to ensure sustainable development for human public health safety.

The invention provides GeXP rapid detection primer set for simultaneously identifying gene HA of eight different human-infected subtypes of avian influenza virus, kit and use thereof.

In order to solve the technical problem, the invention applies the following technical solution:

a GeXP rapid detection primer set for simultaneously identifying gene HA of eight different human-infected subtypes of avian influenza virus, comprises 9 pairs of specific primer and 1 pair of universal primer; the 9 pairs of specific primer are respectively primer pair of A1 and A2, primer pair of B1 and B2, primer pair of C1 and C2, primer pair of D1 and D2, primer pair of E1 and E1, primer pair of F1 and F2, primer pair of G1 and G2, primer pair of H1 and H2, primer pair of I1 and I2; the 1 pair of universal primer is Cy5-Tag-F and Tag-R; the 9 pairs of specific primer and 1 pair of universal primer respectively have the sequences as shown from SEQ ID No.1 to SEQ ID No.20.

A GeXP rapid detection kit for simultaneously identifying gene HA of eight different human-infected subtypes of avian influenza virus, comprises cDNA, 10×PCR buffer, MgCl$_2$, dNTP, Jumpstart Taq polymerase, 9 pairs of specific primer, 1 pair of universal primer and RNA-free water, the 9 pairs of specific primer and 1 pair of universal primer respectively have the sequences as shown from SEQ ID No.1 to SEQ ID No.20.

Preferably, the molar concentrations of the 9 pairs of specific primer pair of A1 and A2, primer pair of B1 and B2, primer pair of C1 and C2, primer pair of D1 and D2, primer pair of E1 and E2, primer pair of F1 and F2, primer pair of G1 and G2, primer pair of H1 and H2, and primer pair of I1 and I2 present in PCR reaction system are respectively 150 nmol/L, 100 nmol/L, 100 nmol/L, 150 nmol/L, 100 nmol/L, 100 nmol/L, 100 nmol/L, 100 nmol/L and 100 nmol/L; the molar concentrations of the universal primer pair of Cy5-Tag-F and Tag-R present in PCR reaction system are 500 nmol/L.

Preferably, total volume of the kit is 25 μL/tube, wherein the kit comprises: cDNA 2.0 μL, 10×PCR buffer 2.5 μL, MgCl$_2$ 2.5 μL, dNTP 1 μL, Jumpstart Taq polymerase 1.2 μL, mixture of 9 pairs of specific primers 1.25 μL, mixture of upstream and downstream universal primers 1.25 μL, RNA-free water complemented to 25 μL.

The present invention also provides use of a GeXP rapid detection primer sets for simultaneously identifying gene HA of eight different human-infected subtypes of avian influenza virus or a GeXP rapid detection kit for simultaneously identifying gene HA of eight different human-infected subtypes of avian influenza virus for identification of subtypes H1, H2, H3, H5, H6, H7, H9 and H10 of avian influenza virus.

Compared with the prior art, the present invention has the following beneficial effects:

1. The present invention uses GenomeLab™ GeXP genetic analysis system to establish a method of multiplex reverse transcription polymerase chain reaction (mRT-PCR) which can simultaneously detect gene HA of eight different human-infected subtypes of avian influenza virus from the nine genes of M, H1, H2, H3, H5, H6, H7, H9 and H10. Reaction conditions and multiplex reaction system were optimized first, and then the specificity of multiplex PCR system was verified with verified positive templates respectively. Multiplex detection system can simultaneously detect eight different human-infected subtypes of avian influenza virus, with sensitivity of 10$^2$ copies/μL. The method has advantages of high throughput, strong specificity, high sensitivity and fast speed, which is of great significance for the epidemiological investigation and differential diagnosis of different human-infected subtypes of avian influenza virus.

2. The GeXP multiplex PCR technique established in the present invention provides a method of multiplex reverse transcription polymerase chain reaction (mRT-PCR) which can simultaneously detect gene HA of eight different human-infected subtypes of avian influenza virus from the nine genes of M, H1, H2, H3, H5, H6, H7, H9 and H10 by one PCR reaction in four hours. The method is used to detect eight different subtypes HA of avian influenza virus and perform genotyping thereof for the goal of rapid diagnosis and discrimination of different humans-infected subtypes of avian influenza virus. The method has great significance for the epidemiological investigation of human-infected avian influenza virus, prevention and control thereof, and it is also important to ensure sustainable development for human public health safety.

BRIEF DESCRIPTION OF THE DRAWINGS

The description of figures: horizontal ordinate—base number of PCR amplification product; longitudinal ordinate—fluorescence signal value.

DETAILED DESCRIPTION

According to embodiments, the present invention is further described in detail, but the implementation methods of the invention are not limited to the scope of the embodiments. These embodiments are used only to illustrate the present invention, rather than to limit the scope of the present invention. In addition, after reading the contents of the invention, a person skilled in the art can make various modifications to the invention, and equivalent change also falls within the scope of the invention.

Experimental methods used in the following embodiments are all common methods if no special description is given. Materials and reagents etc. used in the following embodiments can all be obtained in the business approach, if no special description is given. Avian influenza virus strains and other avian virus reference strains used in the embodiments are all preserved by Guangxi veterinary research institute.

Embodiment 1: Multiplex RT-PCR Primer Design for Avian Influenza Virus

After reviewing related literatures, sequences of nine genes M, H1, H2, H3, H5, H6, H7, H9 and H10 of avian influenza virus were downloaded from GenBank database. DNAStar was used to analyze and compare each nucleotide sequence of gene so as to find conserved regions suitable for specific primer design. Specific primers for nine genes of avian influenza virus were designed with GeXP express profiler tool (see Table 1). Designed primers were analyzed and screened with Primer Premier 5, NCBI PrimerBlast and Oligo7.0, and then 5' ends of all the forward primers and reverse primers were added respectively with non-homologous unique sequence to be universal primers (Uni-Primer). 5' end of upstream universal primer was labeled with fluorescent dye Cy5, namely Cy5-Tag-F, synthesized by Shanghai Invitrogen Company and purified with HPLC.

TABLE 1 primer imformation

| Number | Primer name | Primer sequence (5'-3') | Sequence table number | Amplification size (bp) | Target gene |
|---|---|---|---|---|---|
| A | A1 | AGGTGACACTATAGAATAAGCCGAGATCGCGCAGA | SEQ ID No. 1 | 192 | M |
|   | A2 | GTACGACTCACTATAGGGACGCTCACTGGGCACGGT | SEQ ID No. 2 |   |   |
| B | B1 | AGGTGACACTATAGAATACCAGAAYGTGCATCCTATCACT | SEQ ID No. 3 | 198 | H1 |
|   | B2 | GTACGACTCACTATAGGGATATCATTCCTGTCCAWCCCCCT | SEQ ID No. 4 |   |   |
| C | C1 | AGGTGACACTATAGAATATTCGAGAAAGTRAAGATTYTGCC | SEQ ID No. 5 | 152 | H2 |
|   | C2 | GTACGACTCACTATAGGGA CCAGACCATGTTCCTGAAGAA | SEQ ID No. 6 |   |   |
| D | D1 | AGGTGACACTATAGAATATTGCCATATCATGYTTTTTGCTTTG | SEQ ID No. 7 | 131 | H3 |
|   | D2 | GTACGACTCACTATAGGGAAATGCAAATGTTGCACCTAATGTTG | SEQ ID No. 8 |   |   |
| E | E1 | AGGTGACACTATAGAATAGGAAAGTGTAAGAAACGGAACGTA | SEQ ID No. 9 | 223 | H5 |
|   | E2 | GTACGACTCACTATAGGGA CACATCCATAAAGAYAGACCAGC | SEQ ID No. 10 |   |   |
| F | F1 | AGGTGACACTATAGAATA TCTCAAACAAGGCCCCTCTC | SEQ ID No. 11 | 173 | H6 |
|   | F2 | GTACGACTCACTATAGGGA TCCCATTTCGGGCATTAGGC | SEQ ID No. 12 |   |   |
| G | G1 | AGGTGACACTATAGAATAAGAATACAGATTGACCCAGTSAA | SEQ ID No. 13 | 142 | H7 |
|   | G2 | GTACGACTCACTATAGGGA CCCATTGCAATGGCHAGAAG | SEQ ID No. 14 |   |   |
| H | H1 | AGGTGACACTATAGAATAACCATTTATTCGACTGTCGCCT | SEQ ID No. 15 | 118 | H9 |
|   | H2 | GTACGACTCACTATAGGGACATTGGACATGGCCCAGAA | SEQ ID No. 16 |   |   |
| I | I1 | AGGTGACACTATAGAATA AACACGGACACRGCTGA | SEQ ID No. 17 | 167 | H10 |
|   | I2 | GTACGACTCACTATAGGGA ATTGTTCTGGTAWGTGGAAC | SEQ ID No. 18 |   |   |
| J | Cy5-Tag-F | AGGTGACACTATAGAATA | SEQ ID No. 19 | / | / |

In Table 1, degenerate bases R=A/G, D=A/G/T, Y=C/T. Sequence underlined represented the upstream and downstream universal primer sequences. Fluorescent dye Cy5 labeled the upstream universal primer and did not label the downstream primer. According to different pathogen strains actually detected and instrument error of the GeXP system (such as capillary electrophoresis of GenomeLab™ GeXP Genetic Analysis System), actual amplification product length obtained in the detection with the above primer pairs of A-I and GeXP universal primers can fluctuate in the range of 3 bp based on the expected amplification product length.

Embodiment 2: Establishment of Multiplex PCR Detection System 2.1 Preparation for Template and Monoclonal Plasmid Standard Containing Target Gene According to instruction of MiniBEST Viral RNA/DNA Extraction Kit Ver.5.0 (catalog number DV819A) of Takara Company, nucleic acids were extracted from different subtypes (H1-16 and N1-9) of avian influenza virus and other avian viruses, and obtained nucleic acid samples of 50 μL were packed and preserved under −80° C. RT reaction system was build according to instruction of reverse transcriptase (catalog number D2639A) of Takara Company. Obtained RNA samples were performed reverse transcription according to the following reaction system and reaction conditions to obtain cDNA, with DEPC water as a control of total RNA.

Reaction system (25 μL): 5× Reverse Transcriptase Buffer 5 μL, 50 mmol/L Random Primer (9mer) 1 μL, dNTP Mixture (10 mM/L) 2 μL, 40 U Ribonuclease Inhibitor 0.5 μL, 5 U/μL MLV Reverse Transcriptase 0.5 μL, template RNA 1 μg, RNA-free water complemented to 25 μL.

Reverse transcription temperature 42° C. for 1.5 h, preserved under −20° C. Fragments comprising nine target gene regions of M, H1, H2, H3, H5, H6, H7, H9 and H10 were amplified respectively with PCR. Positive PCR products obtained in the amplification were cloned into T-easy vectors to construct the plasmids. Confirmed by sequencing, these nine recombinant plasmids were those in which T-easy vectors were respectively inserted into the above genes, furthermore the above genes were respectively target genes of nine primer pairs of A-F.

2.2 Primers Were Verified Using a Single RT-PCR Method 2.2.1 Single Specific Primer (SP-Primer) was Diluted to Experimental Concentration of 1 μmol/L, Cy5-Tag-F and Tag-R Were Diluted to Experimental Concentration of 10 μmol/L Total reaction volume was 25 μL, and compositions of the system were: cDNA 2.0 μL, 10×PCR buffer 2.5 μL, MgCl$_2$ (25 mM/L) 2.5 μL, Singa Jumpstart Taq polymerase 1.2 μL (2.5 U/μL) (Singa Company, catalogue number: D4184), dNTP (10 mM/L) 1 μL (Takara Company, catalog number: D4030RA), the mixture of specific primers 1.25 μL, the mixture of upstream and downstream universal primers 1.25 μL, RNA-free water complemented to 25 μL finally.

Reaction conditions were: 94° C. for 5 min, then 94° C. for 30s, 55° C. for 30 s, 72° C. for 30 s, 10 cycles; 94° C. for 30 s, 65° C. for 30 s, 10 cycles; 94° C. for 30 s, 55° C. for 30 s, 72° C. for 30 s, 20 cycles; extended at 72° C. for 3 min, placed at 4° C.

2.2.2 Capillary Electrophoresis

Each PCR product obtained with GenomeLab GeXP genetic analysis system was also detected simultaneously with capillary electrophoresis, operation steps thereof were as follows: formamide was used as loading buffer (US Beckman Coulter Company, catalog number: 608082). DNA size standard Kit-400 Base Pairs (US Beckman Coulter Company, catalog number: 608098) were mixed with loading buffer thoroughly at a volume ratio of 1: (80-160). 39 μL of obtained mixed liquid was added into each hole of sample plate, and then PCR product was diluted for 10-100 times, and 1 μL of diluted product was added to sample plate with pipetting and mixing. At last each hole was sealed with a drop of paraffin oil to avoid formamide oxidation and sample evaporation. ⅔ volume of each hole on buffer plate was added with buffer and capillary electrophoresis was performed. Capillary electrophoresis conditions were as follows: capillary heating: temperature 50° C.; denaturation: 90° C., 120 s; sample injection: 2.0 KV, 30 s; separation: 6.0 KV, 35 mM GenomeLab GeXP genetic analysis system was used to determine the actual detection size of amplification fragment obtained with specific primer of each subtype.

Figure 1:
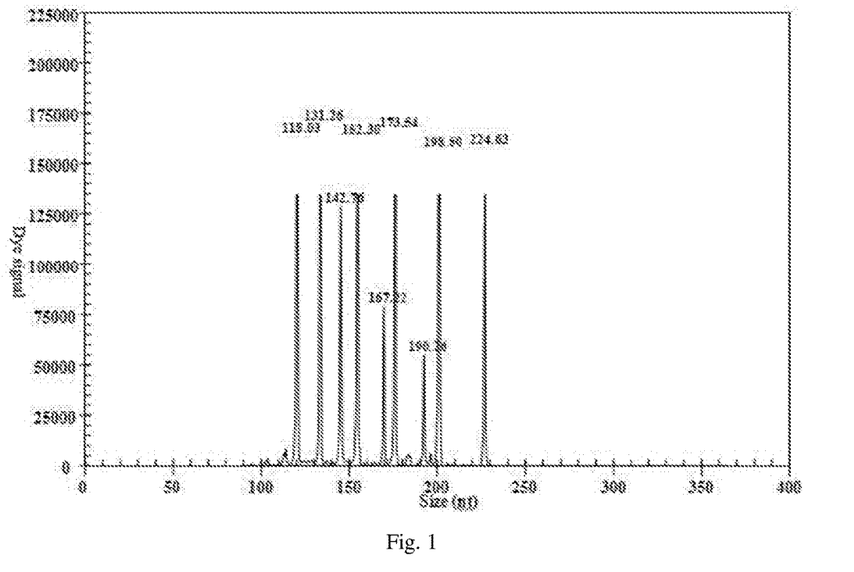
FIG. 1 is capillary electrophoresis analysis diagram for GeXP multiplex PCR.
Figure 2:
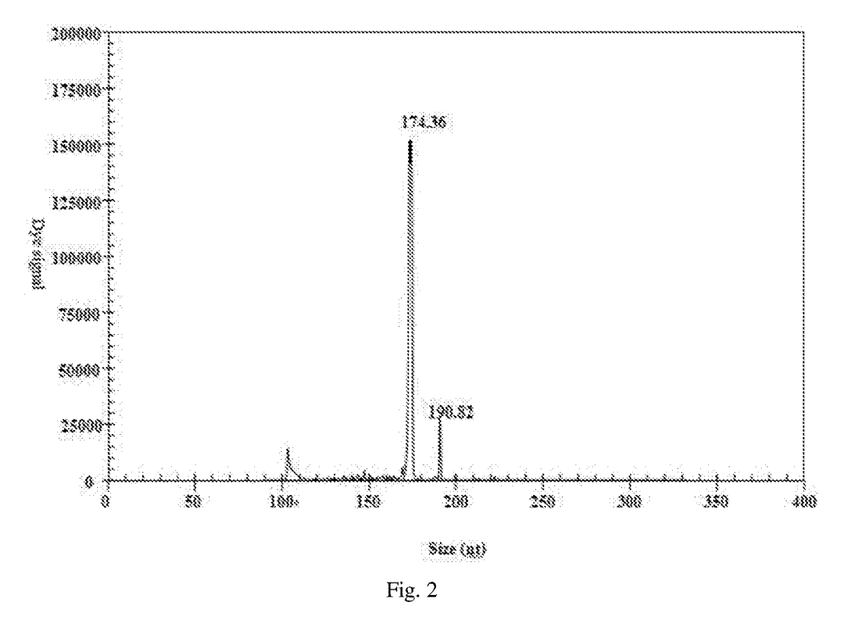
FIG. 2 is detection result of clinical sample infected singly with subtype H6 of avian influenza virus.
Figure 3:
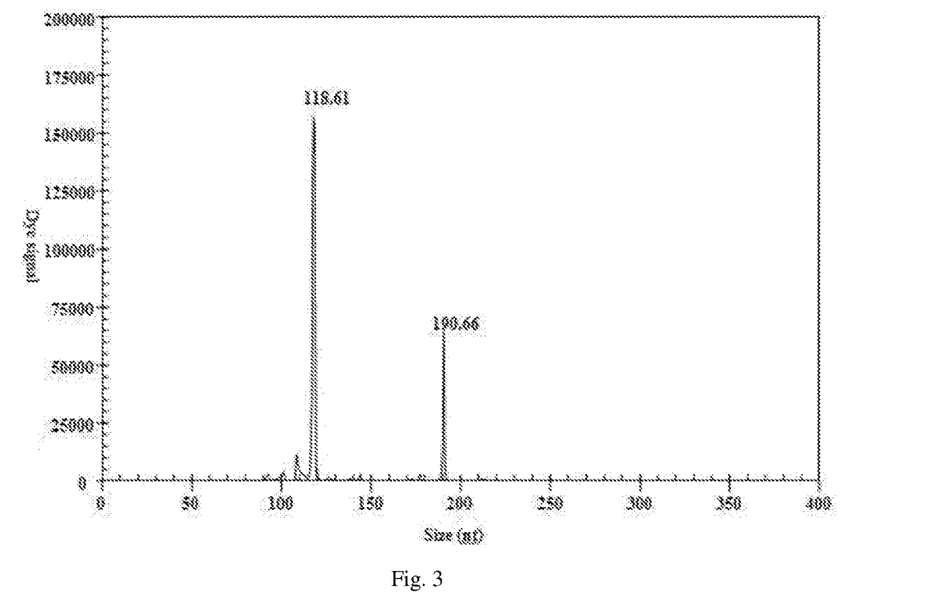
FIG. 3 is detection result of clinical sample infected singly with subtype H9 of avian influenza virus.

2.2.3 Single Specificity Verification of Primer Pairs A-G cDNA samples obtained in Embodiment 1 were amplified respectively with primer pairs A-G: H5N1 was amplified with primer pair A, H1N1 was amplified with primer pair B, H2N3 was amplified with primer pair C, H3N6 was amplified with primer pair D, H5N1 was amplified with primer pair E, H6N8 was amplified with primer pair F, H7N2 was amplified with primer pair G, H9N2 was amplified with primer pair H, H10N3 was amplified with primer pair I. The results of PCR amplification and capillary electrophoresis showed that single specific primers only showed good amplification performance to their target genes and no impurity peak was found. After amplification, different target gene fragments were respectively in the size ranges as follows: AIV M, 190-192 bp; AIV-H1, 197-199 bp; AIV-H2, 152-154 bp; AIV-H3, 131-133 bp; AIV-H5, 222-224 bp; AIV-H6, 173-175 bp; AIV-H7, 141-143 bp; AIV-H9, 117-119 bp; AIV-H10, 166-168 bp.

2.3 Establishment of GeXP Multiplex PCR System

Multiplex mix-primer working liquid was obtained by mixing primer pairs A, B, C, D, E, F, G, H and I. By optimization of primer concentration, the corresponding molar concentrations of the primers of target genes M, H1, H2, H3, H5, H6, H7, H9 and H10 in PCR reaction system were respectively as follows: 150 nmol/L, 100 nmol/L, 100 nmol/L, 150 nmol/L, 100 nmol/L, 100 nmol/L, 100 nmol/L, 100 nmol/L and 100 nmol/L; molar concentration of universal primers Cy5-Tag-F and Tag-R in PCR reaction system was 500 nmol/L. The other components were the same with those used in primer verification. PCR reaction with multiplex primers was performed, in which single positive sample of multiple known viral nucleic acids or mixed cDNA sample of multiple pathogens was used as template. The reaction process and electrophoresis conditions were the same with those used in primer verification.

2.4 Results

Single cDNA or mixed cDNA was detected with 9 primer pairs mixture of primer pairs A-I.

As shown in FIG. 1, the result showed that amplification products of 118.0 bp, 131.2 bp, 142.7 bp, 152.3 bp, 167.2 bp, 173.54 bp, 190.2 bp, 198.5 bp and 224.6 bp were respectively detected with multiple primers and multiple templates, and no amplification product was detected in the negative control. The result obtained with multiple primers and multiple templates showed that nine target genes can be detected simultaneously, and nine target peaks consistent with the actual situation can be detected and no impurity peak was detected through analysis with GeXP multiplex detection system. At the same time, major epidemic subtype of detected avian influenza virus can be distinguished by product fragment size. The results also verified the primer specificity in the multiplex detection system.

Embodiment 3: Specificity Verification of GeXP Multiplex Detection System

Nucleic acids of subtypes HA (1-16) and NA (1-9) of avian influenza virus, and nucleic acids of common avian virus like IBV, NDV and ILTV etc. were extracted respectively from allantoic fluid according to instruction of MiniBEST Viral RNA/DNA Extraction Kit Ver.5.0 and then added respectively to the GeXP multiplex detection system established in Embodiment 2 so as to verify the specificity of this method. After multiplex PCR, PCR product was analyzed by GeXP capillary electrophoresis. The result showed that there was only specific signal in each reaction, and no cross reaction was observed. NDV, IBV, ILTV, blank control and other subtypes HA of Gene HA except H1, H2, H3, H5, H6, H7, H9 and H10 had no reaction signal, suggesting that the method established has a strong specificity, and does not have any cross reaction with other detected objects.

Embodiment 4: Sensitivity Detection Analysis of GeXP Multiplex Detection System and Ability Analysis of GeXP Multiplex Detection System to Detect Clinical Sample 4.1 Sensitivity Detection of GeXP Multiplex Detection System Plasmids comprising respectively genes M, H1, H2, H3, H5, H6, H7, H9 and H10 which were constructed in Embodiment 2 were enzymatically digested with SpeI and PvuII according to instruction of RiboMAX™ Large Scale RNA Production System-T7 Kit (catalog number P1300) of Promega Company, and these above nine linearized plasmids containing different target genes were transcribed in vitro to synthesize RNA. Concentration of RNA obtained by the transcription in vitro was measured and quantified with DU 800 UV/Vis spectrophotometer. Copy number of RNA was calculated according to concentration and molecular weight of the nucleic acid. RNA obtained by the respective transcription of genes M, H1, H2, H3, H5, H6, H7, H9 and H10 in vitro was mixed in the same proportion and obtained mixture was processed with serial dilution to $10^{6}$−10 copies/μL. Diluted products were used as detection samples, sensitivity detection and analysis of GeXP multiplex detection system were performed in the method established in the Embodiment 2. The experiment was repeated 3 times on different days.

Results of 3 repeated experiments showed that this method can detect nucleic acid sample for genes M, H1, H2, H3, H5, H6, H7, H9 and H10 at a minimum of 100 copies/μL.

4.2 The Ability of GeXP Multiplex Detection System to Detect Clinical Sample cDNA of major epidemic subtype of avian influenza virus was randomly selected from Embodiment 1, and detected in the method of step 2 of Embodiment 2.

Detection result of clinical sample infected singly with subtype H6 of avian influenza virus was shown as FIG. 2, two target peaks of 174.36 and 190.82 can be detected simultaneously and no other impurity peaks were found, which showed that the sample only comprised template for subtype H6 of avian influenza virus, coinciding with the actual situation.

Detection result of clinical sample infected singly with subtype H9 of avian influenza virus was shown as FIG. 3, two target peaks of 118.6 and 190.66 can be detected simultaneously and no other impurity peaks were found, which showed that the sample only comprised template for subtype H9 of avian influenza virus, coinciding with the actual situation.

Figure 4:
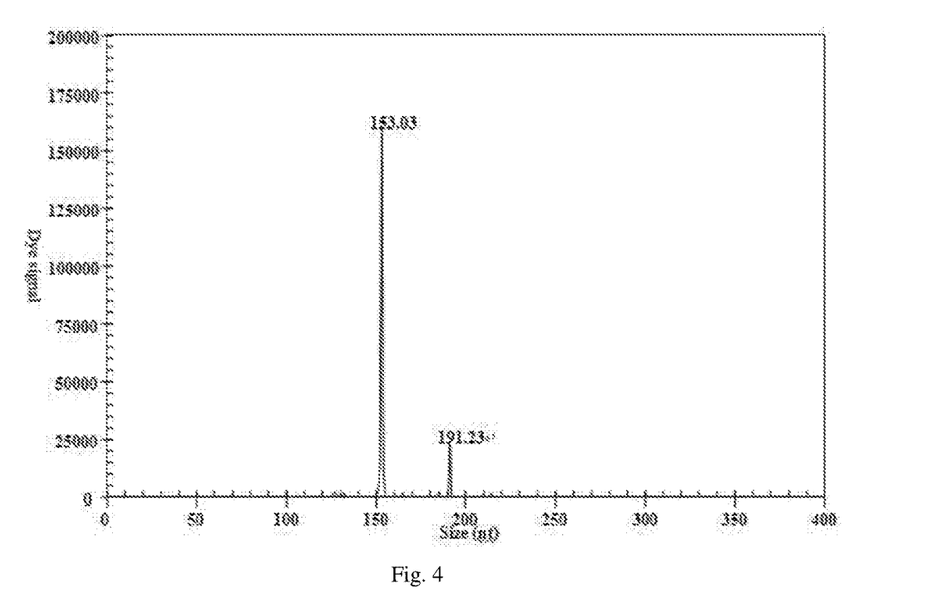
FIG. 4 is detection result of clinical sample infected singly with subtype H2 of avian influenza virus.

Detection result of clinical sample infected singly with subtype H3 of avian influenza virus was shown as FIG. 4, two target peaks of 153.03 and 190.9 can be detected simultaneously and no other impurity peaks were found, which showed that the sample only comprised template for subtype H2 of avian influenza virus, coinciding with the actual situation.

The above specific embodiments of the present invention are for the purpose of illustration. These descriptions do not intend to limit the present invention to the exact form of the disclosure, and it is obvious that various changes and modifications can be carried out according to the above-mentioned teachings. The purpose of selecting and describing these exemplary embodiments is to explain the specific principles and practical application of the present invention, which makes a person skilled in the art achieve and use different exemplary embodiments, selections and changes of the present invention. The scope of the present invention is defined by the claims and its equivalent form.

---

The invention claimed is:

1. A rapid detection primer set for simultaneously identifying gene hemagglutinin (HA) of eight different human-infecting subtypes of avian influenza virus, comprising 9 pairs of specific primer and 1 pair of universal primer; the 9 pairs of specific primer being respectively primer pair of SEQ ID NO. 1 and SEQ ID NO. 2, primer pair of SEQ ID NO. 3 and SEQ ID NO. 4, primer pair of SEQ ID NO. 5 and SEQ ID NO. 6, primer pair of SEQ ID NO. 7 and SEQ ID NO. 8, primer pair of SEQ ID NO. 9 and SEQ ID NO. 10, primer pair of SEQ ID NO. 11 and SEQ ID NO. 12, primer pair of SEQ ID NO. 13 and SEQ ID NO. 14, primer pair of SEQ ID NO. 15 and SEQ ID NO. 16, primer pair of SEQ ID NO. 17 and SEQ ID NO. 18; and, the 1 pair of universal primer being SEQ ID NO. 19 and SEQ ID NO. 20.

2. A rapid detection kit for simultaneously identifying gene HA of eight different human-infecting subtypes of avian influenza virus, comprising cDNA, 10×PCR buffer, MgCl$_2$, dNTP, Taq polymerase, 9 pairs of specific primer, 1 pair of universal primer and RNA-free water, the 9 pairs of specific primer and 1 pair of universal primer respectively having the sequences as shown from SEQ ID No.1 to SEQ ID No.20.

3. A multiplex method for detecting subtypes H1, H2, H3, H5, H6, H7, H9, and H10 of avian influenza virus comprising performing a multiplex polymerase chain reaction of a nucleic acid sample with 9 specific primers and one universal primer pair, wherein the 9 pairs of specific primer being respectively primer pair of SEQ ID NO. 1 and SEQ ID NO. 2, primer pair of SEQ ID NO. 3 and SEQ ID NO. 4, primer pair of SEQ ID NO. 5 and SEQ ID NO. 6, primer pair of SEQ ID NO. 7 and SEQ ID NO. 8, primer pair of SEQ ID NO. 9 and SEQ ID NO. 10, primer pair of SEQ ID NO. 11 and SEQ ID NO. 12, primer pair of SEQ ID NO.13 and SEQ ID NO.14, primer pair of SEQ ID NO.15 and SEQ ID NO. 16, primer pair of SEQ ID NO. 17 and SEQ ID NO.18; and, the 1 pair of universal primer being SEQ ID NO. 19 and SEQ ID NO. 20 to generate an amplification product; and analyzing the amplification product to detect the avian influenza virus subtype.

* * * * *